United States Patent
Martin et al.

[11] Patent Number: 5,694,806
[45] Date of Patent: Dec. 9, 1997

[54] MEASUREMENT OF WATER CONTENT

[75] Inventors: Charles Martin; Neil Bonnett Graham, both of Glasgow, United Kingdom

[73] Assignee: University of Strathclyde, Glasgow, United Kingdom

[21] Appl. No.: 564,123

[22] PCT Filed: Jun. 24, 1994

[86] PCT No.: PCT/GB94/01369

§ 371 Date: Jan. 19, 1996

§ 102(e) Date: Jan. 19, 1996

[87] PCT Pub. No.: WO95/00830

PCT Pub. Date: Jan. 5, 1995

[30] Foreign Application Priority Data

Jun. 24, 1993 [GB] United Kingdom ............ 9313017

[51] Int. Cl.⁶ .................................................. G01N 19/10
[52] U.S. Cl. ..................................... 73/73; 73/335.11
[58] Field of Search ........................ 73/73, 335.11, 73/335.13, 335.14

[56] References Cited

U.S. PATENT DOCUMENTS

| | | | |
|---|---|---|---|
| 1,523,322 | 1/1925 | Walton | 73/335.11 |
| 1,690,672 | 11/1928 | Dunlap | 73/73 |
| 2,300,000 | 10/1942 | Mayers | 73/335.11 X |
| 2,573,685 | 11/1951 | Blinn et al. | 73/335.13 |
| 4,069,716 | 1/1978 | Vanasco et al. | 73/432.1 |
| 4,130,012 | 12/1978 | Lockerby et al. | 73/73 |
| 4,655,076 | 4/1987 | Weihe et al. | 73/73 |

FOREIGN PATENT DOCUMENTS

| | | |
|---|---|---|
| 2 522 411 | 9/1983 | France . |
| 0030743 | 2/1988 | Japan ............... 73/73 |
| 0030744 | 2/1988 | Japan ............... 73/73 |
| 0085742 | 3/1990 | Japan ............... 73/73 |
| 453662 | 9/1936 | United Kingdom . |
| 2 017 868 | 10/1979 | United Kingdom . |
| 2 047 093 | 11/1980 | United Kingdom . |
| 2 276 627 | 10/1994 | United Kingdom . |
| 89/11787 | 12/1989 | WIPO . |
| 9 000 248 | 2/1990 | WIPO . |

OTHER PUBLICATIONS

Hydrogels in Medicine and Pharmacy, vol. II: Polymers, Chapter 4, "Poly(ethylene Oxide) And Related Hydrogels", by N.B. Graham, pp. 95–113, 1987.
Patent Abstract of Japan—Patent No. A 60070339, dated Apr. 22, 1985, for "Water Concentration Meter".
Patent Abstract of Japan—Patent No. A 62288524, dated Dec. 15, 1987, for "Water Contact Display Substance".
Database WPI, Section EI, Week 8333, Derwent Publications Ltd., London, GB, Abstract of U.S. Patent 4,511,477 and EP 217791.
Abstract—SU 966,571, 15 Oct. 1982, for "Soil humidity sensor—has cavity filled with swelling material, monitoring moisture–content of soil".
Abstracts—U.S. Patent 4,511,477, Issued Apr. 16, 1985; and EPO–217791, Issued Mar. 7, 1990—"Absorption of acidic aq. media—by use of a water–swellable polymer contg. alkali metal sulphonate groups".
Abstract—Publication No. JP62288524, publication date Dec. 15, 1987—"Water Contact Display Substance".
Abstract—Publication No. JP60070339, publication date Apr. 22, 1985—"Water Concentration Meter".
Abstract—SU–243090, dated Feb. 2, 1981—"Soil Humidity Sensor".

Primary Examiner—Michael Brock
Attorney, Agent, or Firm—Bell Seltzer Intellectual Property Law Group of Alston & Bird LLP

[57] ABSTRACT

A device for indicating the water content of a medium into which the device is inserted, and which includes a scale which mounts a body of a water-swellable hydrogel. The scale has marked thereon an indication of water content, such that contact of the hydrogel body with water or moisture in the medium causes a peripheral portion of the hydrogel to expand and such that the position of the expanded peripheral portion in conjunction with the scale indicates the water content of the medium.

13 Claims, 2 Drawing Sheets

MEASUREMENT OF WATER CONTENT

TECHNICAL FIELD

The present invention relates to a device for indicating the water content of a medium, such as soil, peat or a synthetic growth medium. The device may, however, be applied more generally to the determination of water contents of solid, liquid or gaseous media.

BACKGROUND

Over-watering or under watering of house plants is frequently a cause of their ill-health or death. There is thus a need for a simple instrument which can indicate the water content of the soil or other plant growing medium.

Devices which measure water content, for example by conductivity, are known. However, these may be complex to construct, fragile and unreliable.

SUMMARY OF THE INVENTION

The present invention provides a device for indicating the water content of a medium, which comprises:

indicator means having marked thereon an indication of water content;

body of a water-swellable hydrogel; and means for fixing the hydrogel body relative to the indicator means such that swelling of the hydrogel extends a peripheral portion of the hydrogel, the position of the peripheral portion in conjunction with the indicator means indicating the water content of the medium into which the device is placed.

The use of a water-swellable hydrogel which swells in proportion to the amount of water present, in conjunction with a scale or other indicator means to indicate the water content of a medium, allows the construction of a device which is robust and easy to use and which can be made inexpensively.

In a preferred embodiment, the hydrogel is in the form of a column (e.g. 5 to 20 cm long) and the position of the free end of the column is indicative of water content. Thus, the present device may operate on a similar principal as a thermometer in which liquid in a tube expands as temperature increases; the position of the liquid miniscus being indicative of temperature.

The water content may be read directly from the swelling of the hydrogel over an indicator means in the form of a scale, or the swelling can be used indirectly to drive an indicator means such as a pointer. Swelling of the hydrogel can be arranged to operate a switch or other indicating means when a predetermined water content is reached (indicating the need to add water). In one preferred embodiment the hydrogel is arranged to push against an indicator means in the form of a resiliently biased lever such as to move a pointer across the scale. In another embodiment, the hydrogel is arranged to operate in tension and to pull against a resiliently biased lever and move a pointer.

In a particular embodiment swelling of the hydrogel operates a visual indicator means such as a flag which carries a picture (such as a watering can) which indicates the need to add water or not to add water. A flag indicating the need to add water comes into view when water is required, and a flag indicating that no more water is needed comes into view when the medium contains ample water. Many other such indirect indicating means will be known to the skilled man.

In another embodiment, a strip of hydrogel is laminated to another material of lesser or zero water-swellability (in the manner of a bimetallic strip thermostat) such that as the hydrogel swells it causes the laminate to bend over. The degree of bending indicates the water content.

The scale form of indicator means is analogous to the scale of a conventional thermometer and may be marked with bands, zones or graduations (which may be coloured) indicative of water content. Preferably, the scale is printed or is integrally formed from a thermoplastic material, usually by injection moulding or other known techniques.

Usually the hydrogel will be chosen to swell in a proportional manner (e.g. linearly) relative to water content, in which case the scale will be a linear scale. If the hydrogel swells in a non-linear manner then the scale will be suitably chosen to provide the correct water content reading.

Means are provided for fixing the hydrogel body relative to the scale or other indicator means. Usually, this involves fixing one end of a hydrogel column such that a free end of the column is free to move as the hydrogel swells. For protection the hydrogel column may be enclosed within a tube or located within a slot adjacent the scale. In one embodiment, the hydrogel column is located within a tube of transparent material, such as a transparent plastics material. The preferred material is a thermoplastic which is clear and of brilliant appearance. There are a number of such materials known in the art but poly(methyl methacrylate) or polystyrene are particularly well suited. The material may be tinted to highlight colours on the scale, and to protect from damage by ultraviolet light. Alternatively, the tube could be formed of an inorganic glass or other rigid transparent material. The scale may be integrally formed on the outside of the tube or may be a separate component onto which the tube is mounted. In another embodiment, the hydrogel is protected by a clear plastics magnifying lens to facilitate viewing.

Tubes of non-transparent material may also be employed, provided that a slot or other aperture is left such that the position of the free peripheral end of the hydrogel column can be viewed.

The present invention utilises the ability of water to cause swelling in a column or other body of hydrogel material. To improve visibility where the position of the free end of the column has to be viewed, it is preferred that the hydrogel is coloured so that it can be clearly seen against the scale.

Generally, free access to the hydrogel must be provided, such that water vapour or liquid water in the medium is able to contact the hydrogel body so as to be absorbed by the hydrogel. Thus, where a hydrogel column is contained within a tube of transparent material, it would generally be necessary to provide apertures, such as slots or holes, in the tube in order to allow access of water to the hydrogel. Alternatively, the hydrogel could be arranged to be in direct contact with the surrounding medium.

Water-swellable hydrogels are a known class of materials and are known for many uses (see for example patent specifications GB2047093 and WO90/09168). In the device of the present invention, the swellability defined as the maximum volume increase on swelling to equilibrium in water is preferably less than ten times (e.g. 1 to 6 times, preferably 2 to 5 times) the dry volume of the hydrogel at room temperature of 20° C. Otherwise, swollen hydrogels which are weak and have insufficient mechanical strength may be obtained. Moreover since hydrogels in general tend to swell uniformly in all directions, if a hydrogel of too large a swelling capacity is employed, there is a danger that the hydrogel body may become jammed in its container due to lateral expansion. The term "hydrogel" includes gels in the dry (xerogel) and hydrated state.

The hydrogel is preferably a tough material in the dry state, such as to avoid problems of distortion and stress cracking. Hydrogels which are brittle in the dry state are not preferred since they may become cracked on swelling. The hydrogel should generally be capable of repeated swelling and contraction without degradation of its physical properties or change in its swellability.

Preferably, the Young's modulus of the hydrogel exceeds 2 $MNm^{-2}$ (preferably in excess of 5 $NMm^{-2}$) in the dry state; and in the swollen state preferably exceeds 0.7 $MNm^{-2}$ (particularly in excess of 1.8 $MNm^{-2}$). Generally the ultimate stress exceeds 4 $NMm^{-2}$ (preferably exceeds 10 $NMm^{-2}$) in the dry state; and in the swollen state preferably exceeds 7 $NMm^{-2}$ (particularly in excess of 18 $MNm^{-2}$.

The degree of swelling of the hydrogel material is proportional to the water-content and is preferably substantially independent of factors such as the pH content or the salt content of the water, such that changes in these parameters do not give a false reading of water content.

Where the device is to measure the water content of a solid medium such as soil, part of the hydrogel will be inserted into the soil leaving the free end of the hydrogel out of the medium so that its position can be read. Generally 30-70% of the hydrogel is inserted into the medium, and a mark at the chosen depth may be provided on the device to facilitate insertion to the correct depth. In the case of soil, insertion to a depth of at least 2 cm is usually required in order to get suitable water uptake. The depth may vary from summer to winter to reflect the different water requirements of the plant throughout the year, for example there may be two depth marks, one for summer and one for winter.

In another embodiment, the hydrogel body extends substantially in two dimensions (e.g. as a circle, oval, square, triangle etc.) and the outward expansion of the periphery moving over a corresponding scale indicates water content.

The hydrogel may be mounted on a wick to draw water from the surrounding medium into contact with the hydrogel.

Preferred hydrogels according to the present invention are those based on poly(ethylene oxide) which has been converted into a form which will swell but not dissolve in water, usually by one of the following processes: chemical cross-linking, including cross-linking by irradiation, entanglement cross-linking, conversion into a suitable block or graft copolymer or chemical complexation. Such materials are well known to those skilled in the art and are, for example, discussed in "Poly(ethylene oxide) and related Hydrogels", Chapter 4, "Hydrogels in Medicine and Pharmacy" Volume II, Polymers, 1987, pages 95 to 113 CRC Press, N. B. Graham. Isocyanate terminated poly(ethylene oxide) polymers available under the trademark HYPOL (W. R. Grace) are especially useful for production of the hydrogel. The hydrogel polymer may be a linear random block copolymer comprising segments of poly(ethylene oxide) and poly (propylene oxide) connected by polyurethaneurea hydrophobic segments formed from the reaction of a diisocyanate and a diamine. Conventional additives such as antioxidants, UV absorbers etc. may be included.

The device may also be used to measure relative humidity of the atmosphere. It may include maximum and minimum indicators analogous to maximum and minimum thermometers.

DESCRIPTION OF PREFERRED EMBODIMENTS

Figure 1:
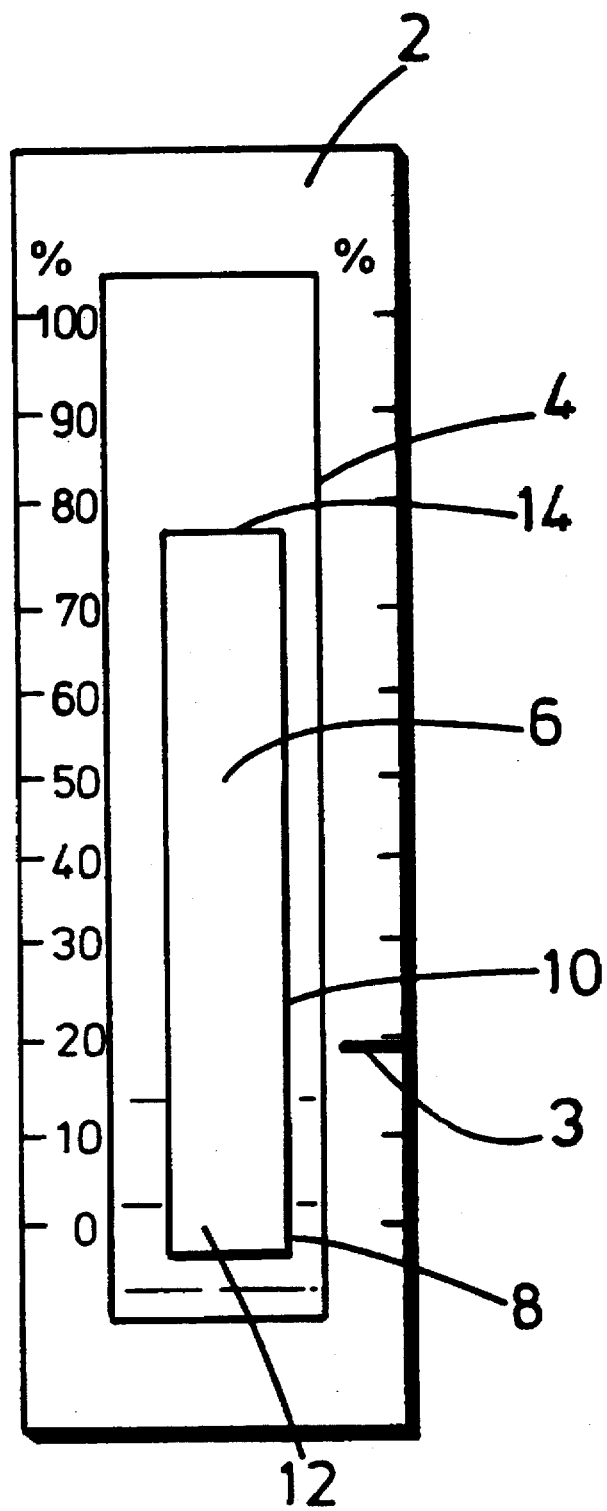
Figure 2:
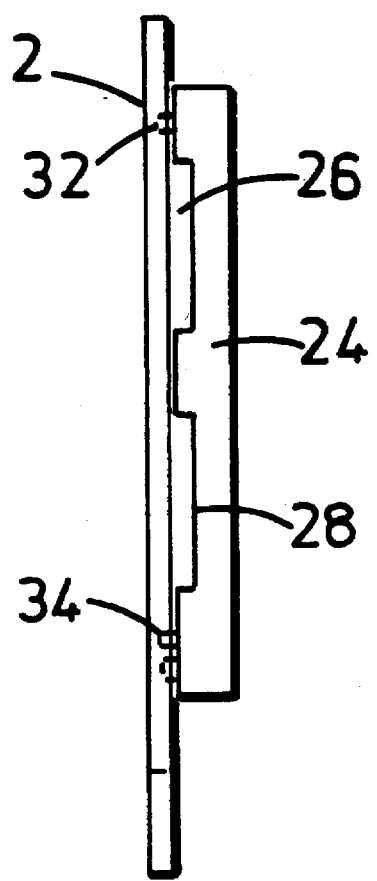
Figure 3:
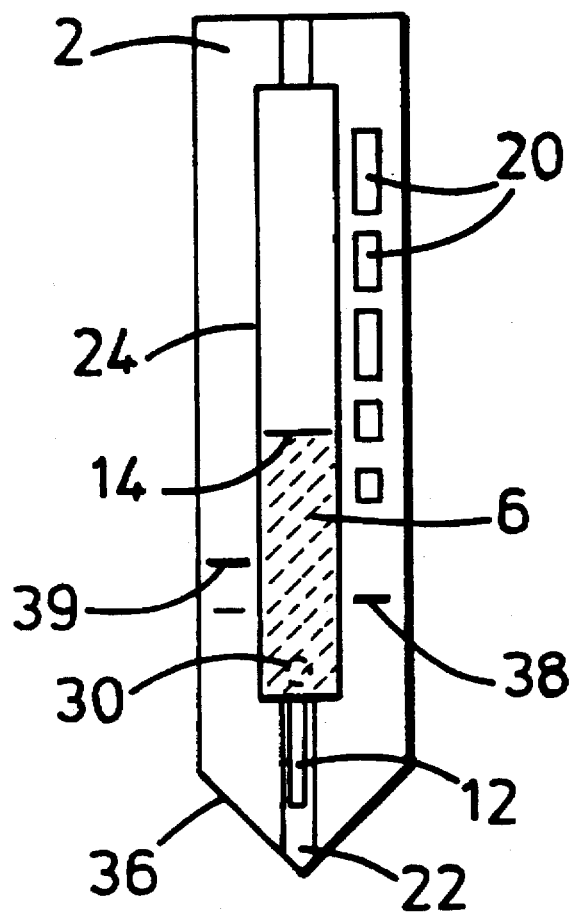
Figure 4:
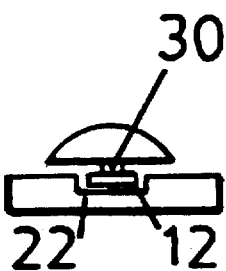

Embodiments of the present invention will now be described by way of example only with reference to the drawing wherein;

FIG. 1 is a schematic elevation of a device according to the present invention; and FIGS. 2,3 and 4 show respectively a side elevation, front elevation and end elevation of a further embodiment employing a magnifying lens.

FIG. 1 shows a device for measuring the water content of a semi-solid medium such as a plant growing medium. The device could, of course, be used for measuring the water content of other flowable media such as granules, particles etc., (for example sand, gravel or other particulate material). The device is even suitable for measuring the water content of a liquid or a gas provided it does not interact with the hydrogel. Thus, it could be used to measure the relative humidity of air.

The device comprises a scale 2, which could be formed of plastics, wood, metal or other suitable material having integrally formed or marked thereon a series of graduations indicative of percentage water content. A depth marker 3 indicates the depth to which the device is to be inserted into the medium to be tested. Affixed to the front of the scale (or set into the scale) is a transparent tube 4, closed at a lower end and open at its upper end. The tube is formed from poly(methylmethacrylate) or polystyrene. The tube includes a series of apertures 10 to allow transmission of water or water vapour from the surrounding medium to the interior of the tube.

A rod 6 of a water-swellable hydrogel, usually a poly (ethylene oxide), is located inside the tube. The poly (ethylene oxide) is typically a linear random block copolymer comprising segments of poly(ethylene oxide) and poly (propylene oxide) connected by polyurethaneurea segments. The lower end 12 of the hydrogel is embedded in a resin 8, such as to fix the lower end of the hydrogel in place, whilst allowing the remainder of the hydrogel to expand as it becomes hydrated.

The device is particularly suitable for giving a continuous long term indication of the water content of a growing medium such as soil, and may be used as follows. The lower end of the device is pushed into the soil up to the depth marker so as to be in intimate contact with the soil, yet at the same time allow the scale to be read. Water or water vapour from the soil enters the transparent tube through the apertures 10 and becomes absorbed by the hydrogel 6. This causes swelling of the hydrogel in proportion to the amount of water taken up by the hydrogel, until the water vapour pressure inside the tube equals that in the soil. The device is left for a period of time to eguilibrate, usually from 1 to 12 hours. The hydrogel is dyed so as to be more easily visible and the position of the upper end 14 of the hydrogel column indicates the percentage water content of the medium.

The device is simple to use, inexpensive and robust.

The device shown in FIGS. 2 to 4 comprises a scale 2 provided with coloured bands 20 indicative of different water contents e.g. for different plant types. The scale includes a channel 22 into which a hydrogel column 6 is located. A magnifying semi-cylindrical plastics lens 24 having cutouts 26, 28 at the rear to allow access of water is clipped over the hydrogel column. A nib 30 traps the lower end 12 of the hydrogel in place. Integrally moulded clips 32,34 clip into apertures in the scale 2 to fix the lens in place. The device has a pointed end 36 for insertion into the soil up to a depth marker 38. An additional depth marker 39 for winter use may be provided.

The device is used substantially in the manner described above.

The position of the upper end of the hydrogel column, magnified by means of the lens, indicates the water content of the soil by reference to one of the coloured bands. In FIG.

3 the water content corresponds to the second band from the bottom. Water may be given to the plant, as required to provide the optional water content of the soil for that particular plant type.

We claim:

1. A device for indicating the water content of a medium, which comprises:

a scale provided with a channel and having marked thereon an indication of water content which extends along the channel;

a body comprising a water-swellable hydrogel; and means fixing the hydrogel body to the scale and within said channel, such that swelling of the hydrogel extends a peripheral portion of the hydrogel along the length of the channel, the position of the peripheral portion in conjunction with the indication of water content on the scale indicating the water content of the medium into which the device is placed.

2. A device according to claim 1 wherein the hydrogel is a linear random block copolymer comprising segments of poly(ethylene oxide) and poly(propylene oxide) connected by polyurethaneurea segments.

3. A device according to claim 1 wherein the swellability of the hydrogel in water is from 2 to 5 times the dry volume of the hydrogel.

4. A device according to claim 1 wherein the swellability of the hydogel is substantially unaffected by changes in pH or salt content of the water.

5. A device according to claim 1 wherein the scale includes a plurality of bands (20), each band being indicative of different water content ranges for different types of plant.

6. A device according to claim 1 which further comprises a depth marker (38, 39) adjacent a lower end portion of the device for determining the depth to which the lower end portion is to be inserted into the medium.

7. A device according to claim 1 wherein the hydrogel is coloured.

8. A device according to claim 1 which further comprises magnification means for magnifying the peripheral portion of the hydrogel body.

9. A device according to claim 1 wherein the scale is integrally molded, and further comprising a plastic magnifying lens located over the hydrogel body and means in the form of a nib fixing a lower end portion of the hydrogel body in the channel.

10. A device according to claim 1 wherein the hydrogel body comprises a poly (ethylene oxide).

11. A device according to claim 1 wherein the scale is integrally molded.

12. A device according to claim 1 further comprising a magnifying lens mounted on the scale so as to overlie the hydrogel body.

13. A device according to claim 12 further comprising means fixing a lower end portion of the hydrogel body in the channel.

* * * * *